US012620087B2

(12) United States Patent
Alam

(10) Patent No.: US 12,620,087 B2
(45) Date of Patent: May 5, 2026

(54) DIANET: A DEEP LEARNING BASED ARCHITECTURE TO DIAGNOSE DIABETES USING RETINAL IMAGES ONLY

(71) Applicant: Qatar Foundation for Education, Science and Community Development, Doha (QA)

(72) Inventor: Tanvir Alam, Doha (QA)

(73) Assignee: HAMAD BIN KHALIFA UNIVERSITY, Doha (QA)

( * ) Notice: Subject to any disclaimer, the term of this patent is extended or adjusted under 35 U.S.C. 154(b) by 493 days.

(21) Appl. No.: 18/094,649

(22) Filed: Jan. 9, 2023

(65) Prior Publication Data

US 2023/0222650 A1     Jul. 13, 2023

Related U.S. Application Data

(60) Provisional application No. 63/298,473, filed on Jan. 11, 2022.

(51) Int. Cl.
| | |
|---|---|
| *G06K 9/00* | (2022.01) |
| *A61B 5/00* | (2006.01) |
| *G06N 3/098* | (2023.01) |
| *G06T 3/40* | (2006.01) |
| *G06T 7/00* | (2017.01) |
| *G06T 7/11* | (2017.01) |
| G06N 3/0464 | (2023.01) |

(52) U.S. Cl.
CPC .......... *G06T 7/0012* (2013.01); *A61B 5/7267* (2013.01); *A61B 5/7275* (2013.01); *G06N 3/098* (2023.01); *G06T 3/40* (2013.01); *G06T*

*7/11* (2017.01); *G06N 3/0464* (2023.01); *G06T 2207/20081* (2013.01); *G06T 2207/20084* (2013.01); *G06T 2207/20132* (2013.01); *G06T 2207/30041* (2013.01)

(58) Field of Classification Search
CPC ........... G06T 2207/30041; G06T 2207/20084
See application file for complete search history.

(56) References Cited

U.S. PATENT DOCUMENTS

| | | | |
|---|---|---|---|
| 10,257,487 B1 * | 4/2019 | Tamatam | .................. G06T 1/60 |
| 2010/0037059 A1 * | 2/2010 | Sun | .................... H04N 1/32144 |
| | | | 713/176 |

(Continued)

OTHER PUBLICATIONS

Islam, Mohammad Tariqul, et al. "DiaNet: A deep learning based architecture to diagnose diabetes using retinal images only." Ieee Access 9 (2021): 15686-15695. (Year: 2021).*

(Continued)

*Primary Examiner* — Hadi Akhavannik
(74) *Attorney, Agent, or Firm* — K&L Gates LLP

(57) ABSTRACT

A method of training a convolutional neural network model to predict diabetes from an image of a retina is provided. The method of training a convolutional neural network includes processing a first dataset, wherein processing the first dataset comprises: extracting a circular region from a retinal image, resizing the circular region, cropping the circular region, and placing the circular region onto a black background; training an initial model using a second dataset to yield a first model; training the first model using a third dataset to yield a second model; and training the second model using the first dataset to yield a third model.

15 Claims, 4 Drawing Sheets

(56) References Cited

U.S. PATENT DOCUMENTS

| | | | | |
|---|---|---|---|---|
| 2017/0310935 A1* | 10/2017 | Sinclair | B29C 64/245 |
| 2018/0060722 A1* | 3/2018 | Hwang | G06N 3/0895 |
| 2018/0122068 A1* | 5/2018 | Garnavi | G06T 7/0012 |
| 2018/0235467 A1* | 8/2018 | Celenk | A61B 3/14 |
| 2019/0104722 A1* | 4/2019 | Slaughter | A01M 7/0089 |
| 2019/0221313 A1* | 7/2019 | Rim | G06F 18/217 |
| 2020/0058123 A1* | 2/2020 | Liao | G16H 30/20 |
| 2020/0160999 A1* | 5/2020 | Rim | G06T 7/00 |
| 2020/0191553 A1* | 6/2020 | Rothberg | A61B 5/0022 |
| 2020/0193004 A1* | 6/2020 | West | G06N 3/09 |
| 2020/0258215 A1* | 8/2020 | Kashyap | G06N 20/00 |
| 2021/0327062 A1* | 10/2021 | Choi | A61B 5/00 |

OTHER PUBLICATIONS

Kim, K. M., et al. "Development of a Fundus Image-Based Deep Learning Diagnostic Tool for Various Retinal Diseases." J. Pers. Med 11 (2021): 321. (Year: 2021).*

Rajpurkar, Pranav, et al. "Chexnet: Radiologist-level pneumonia detection on chest x-rays with deep learning." arXiv preprint arXiv: 1711.05225 (2017). (Year: 2017).*

Graham; "Kaggle Diabetic Retinopathy Detection competition report"; Aug. 6, 2015; Department of Statistics and Centre for Complexity Science, University of Warwick; (9 pages).

Sisodia, et al.; "Prediction of Diabetes using Classification Algorithms"; ScienceDirect; 2018; (8 pages).

Bora, et al.; "Predicting the risk of developing diabetic retinopathy using deep learning"; Lancet Digit Health 2021; vol. 3, Jan. 2021; (10 pages).

Huang, et al.; "Densely Connected Convolutional Networks"; CVPR; https://openaccess.thecvf.com/content_cvpr_2017/papers/Huang_Densely_Connected_Convolutional_CVPR_2017_paper.pdf; 2017; (9 pages).

* cited by examiner

DIANET: A DEEP LEARNING BASED ARCHITECTURE TO DIAGNOSE DIABETES USING RETINAL IMAGES ONLY

CROSS-REFERENCES TO RELATED APPLICATIONS

The present disclosure claims priority to U.S. Provisional Patent Application 63/298,473 titled "DIANET: A DEEP LEARNING BASED ARCHITECTURE TO DIAGNOSE DIABETES USING RETINAL IMAGES ONLY" having a filing date of Jan. 11, 2022, the entirety of which is incorporated herein.

BACKGROUND

Diabetes is one of the leading fatal diseases globally, putting a huge burden on the global healthcare system. Diabetes mellitus or diabetes is considered a collection of metabolic conditions that can predominantly be described by hyperglycemia rising from the deficiency in insulin discharge. The prolonged hyperglycemia of diabetes is correlated with long-term impairment and collapse of heart, kidneys, and microvascular circulation of the retina. Among diabetic individuals in the USA, almost 30% of them have the tendency of growing diabetic retinopathy, a common complication for diabetic patients, which may lead to blindness. Diabetes may adversely affect the vascular system of the retina causing structural change of it.

As the changes in vascular structure in retina can provide visual cues for diabetes, most clinical guidelines recommend annual retinal screening for diabetic patients through retinal fundus images or dilated eye examinations. Alternatively, these retinal images can be used to detect diabetes, but it requires subjective judgement from the ophthalmologist, and it might be time consuming as well. Automatic retinal image-based diabetes diagnosis in a clinical setting could alleviate the workload of the ophthalmologist as well as screen a large number of patients objectively within a short amount of time.

Current research has been conducted, which include (1) detecting diabetic retinopathy from retinal images and (2) diagnosing of diabetes based on clinical markers e.g., HbA1c, Glucose. However, current research has not addressed the task of detecting diabetes using retinal images from a holistic point of view, independent of the presence of diabetic retinopathy. Thus, improved non-invasive diabetes screening solutions are needed.

SUMMARY

The present disclosure generally relates to a method of training a convolutional neural network model to predict diabetes from the image of a retina.

In light of the present disclosure, and without limiting the scope of the disclosure in any way, in an aspect of the present disclosure, which may be combined with any other aspect listed herein unless specified otherwise, a method of training a convolutional neural network model to predict diabetes from the image of a retina is provided.

In an aspect of the present disclosure, which may be combined with any other aspect listed herein unless specified otherwise, the method of training a convolutional neural network model to predict diabetes from the image of a retina, comprising: processing a first dataset, wherein processing the first dataset comprises: extracting a circular region from a retinal image; resizing the circular region; cropping the circular region; and placing the circular region onto a black background; training an initial model using a second dataset to yield a first model; training the first model using a third dataset to yield a second model; and training the second model using the first dataset to yield a third model.

In an aspect of the present disclosure, which may be combined with any other aspect listed herein unless specified otherwise, processing the first dataset outputs an image having a retina with a radius of 300 pixels.

In an aspect of the present disclosure, which may be combined with any other aspect listed herein unless specified otherwise, the initial model is a DenseNet model.

In an aspect of the present disclosure, which may be combined with any other aspect listed herein unless specified otherwise, the DenseNet model is a 121-layer variant DenseNet model.

In an aspect of the present disclosure, which may be combined with any other aspect listed herein unless specified otherwise, the first dataset comprises a plurality of retinal images including a first group of retinal images and a second group of retinal images.

In an aspect of the present disclosure, which may be combined with any other aspect listed herein unless specified otherwise, the first group of retinal images relates to a control group and the second group of retinal images relates to a diabetes group.

In an aspect of the present disclosure, which may be combined with any other aspect listed herein unless specified otherwise, the third dataset comprises a plurality of retinal images labeled based on the severity of diabetic retinopathy.

In an aspect of the present disclosure, which may be combined with any other aspect listed herein unless specified otherwise, the convolutional neural network model architecture to predict diabetes from an image of a retina, comprises: a DenseNet-121 backbone; and a final layer outputting a predictive label corresponding to a diabetic prediction or a non-diabetic prediction.

In an aspect of the present disclosure, which may be combined with any other aspect listed herein unless specified otherwise, the final layer is a single neuron layer.

In an aspect of the present disclosure, which may be combined with any other aspect listed herein unless specified otherwise, the convolutional neural network model architecture to predict diabetes from an image of a retina further comprises a pair of pooling layers.

In an aspect of the present disclosure, which may be combined with any other aspect listed herein unless specified otherwise, the pair of pooling layers comprises a global average pooling layer and a global max pooling layer.

In an aspect of the present disclosure, which may be combined with any other aspect listed herein unless specified otherwise, the convolutional neural network model architecture to predict diabetes from an image of a retina further comprises a first composite layer, a second composite layer, and a third composite layer.

In an aspect of the present disclosure, which may be combined with any other aspect listed herein unless specified otherwise, the first composite layer comprises a first sequence of a plurality of layers, the second composite layer comprises a second sequence of a plurality of layers, and the third composite layer comprises a third sequence of a plurality of layers.

In an aspect of the present disclosure, which may be combined with any other aspect listed herein unless specified otherwise, the first sequence of the plurality of layers comprises a batch normalization layer, a dropout layer, a linear layer, and a rectified linear unit layer.

In an aspect of the present disclosure, which may be combined with any other aspect listed herein unless specified otherwise, the second sequence of the plurality of layers comprises a batch normalization layer, a dropout layer, a linear layer, and a rectified linear unit layer.

In an aspect of the present disclosure, which may be combined with any other aspect listed herein unless specified otherwise, the third sequence of the plurality of layers comprises a batch normalization layer, a dropout layer, and the final layer for outputting the predictive label.

In an aspect of the present disclosure, which may be combined with any other aspect listed herein unless specified otherwise, the method of training a convolutional neural network model to predict diabetes from the image of a retina, comprises: processing a first dataset and a second dataset, wherein processing the first dataset and the second dataset comprises: extracting a circular region from a retinal image; resizing the circular region; cropping the circular region; and placing the circular region onto a black background; training a DenseNet-121 model using an third dataset to yield a first model; training the first model using the second dataset to yield a second model; and training the second model using the first dataset to yield a third model.

In an aspect of the present disclosure, which may be combined with any other aspect listed herein unless specified otherwise, the third model has an architecture comprising: a DenseNet-121 backbone; a global average pooling layer; a global max pooling layer; a first composite layer; a second composite layer; and a third composite layer.

In an aspect of the present disclosure, which may be combined with any other aspect listed herein unless specified otherwise, the third composite layer comprises: a batch normalization layer, a dropout layer; and a final layer outputting a predictive label corresponding to a diabetic prediction or a non-diabetic prediction.

In an aspect of the present disclosure, which may be combined with any other aspect listed herein unless specified otherwise, the first composite layer comprises: a batch normalization layer; a dropout layer; a linear layer; and a rectified linear unit layer.

The reader will appreciate the foregoing details, as well as others, upon considering the following detailed description of certain non-limiting embodiments including a multilevel power line communication quantization method for physical layer security.

BRIEF DESCRIPTION OF THE DRAWINGS

The accompanying figures depict various elements of the one or more embodiments of the present disclosure, and are not considered limiting of the scope of the present disclosure.

In the Figures, some elements may be shown not to scale with other elements so as to more clearly show the details. Additionally, like reference numbers are used, where possible, to indicate like elements throughout the several Figures.

DETAILED DESCRIPTION

The present disclosure generally relates to a method of training a convolutional neural network model to predict diabetes from the image of a retina.

According to an embodiment of the present disclosure, a method of training a convolutional neural network model to predict diabetes from the image of a retina uses at least one data set. In an example embodiment, the method uses a first dataset and a second dataset.

The first dataset ("the QBB dataset") consists of retinal images from a diabetes cohort of size 246 and a control group of size 246. To obtain the first dataset, medical practitioners interviewed each participants to collect their medical and family history, lifestyle, and their habitual factors. Then, both the diabetes and the control groups were determined with the help of medical practitioners and nurses. The diabetes group was free from self-reported diabetic status or the HbA1c % was greater or equal to 6.5 percent. The control group was free from diabetes, obesity, and cardiovascular disease. All the subjects from the cohort were Qatari nationals, and the cohort was evenly distributed based on male and female gender for both groups. Thus, the cohort was comprised of 50 percent males and 50 percent female. A Topcon TRC-NW6S retinal camera was used to capture features of the optic nerve and macula from each participants.

Figure 1:
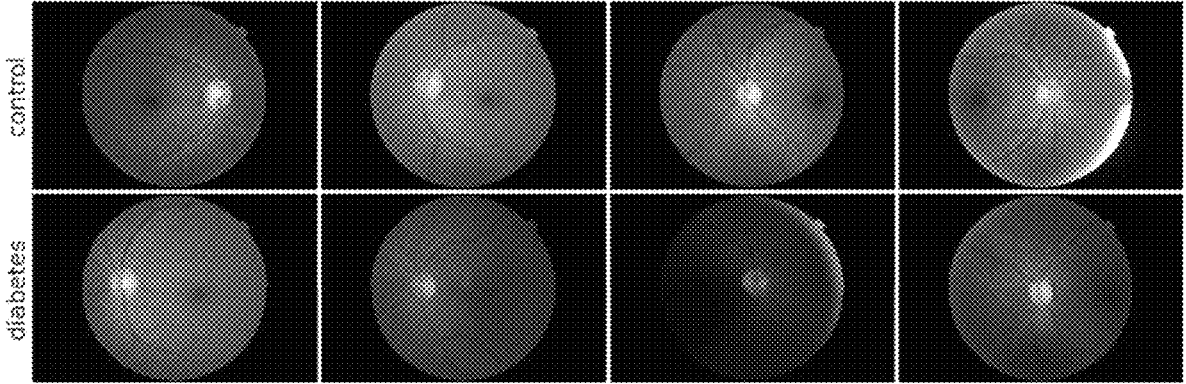
FIG. 1 illustrates an example set of retinal images from the QBB dataset.
Figure 2:
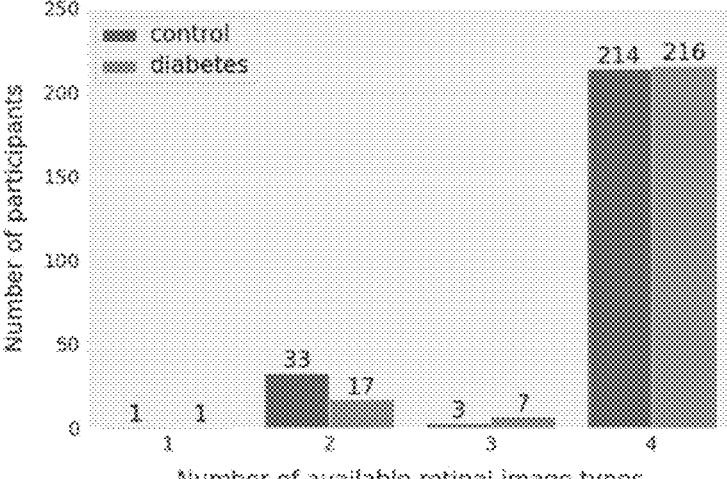
FIG. 2 illustrates a bar graph representing the number of participants with each of the four types of image availability configuration: (left, right) (macula-centered, disc-centered) from the QBB dataset.

The QBB dataset does not evaluate or grade diabetic retinopathy for any of the participants. Thus, the participants from within the QBB dataset may or may not have diabetic retinopathy. Further, the QBB dataset does not contain the same number of images for each participant. At most, there were types of images from the left and right eyes: (a) macula-centered images, and (b) disc-centered images. The QBB dataset includes 1852 images from 492 participants. The mode of the original image sizes was 3696 by 2448 pixels. FIG. 1 shows randomly selected example images from the QBB dataset with the top row corresponding to images taken of the control group and the bottom row corresponding to images taken of the diabetes group. FIG. 2 is a graphical representation of the QBB dataset with the number of available retinal images on the x-axis and the number of participates on the y-axis.

Figure 3:
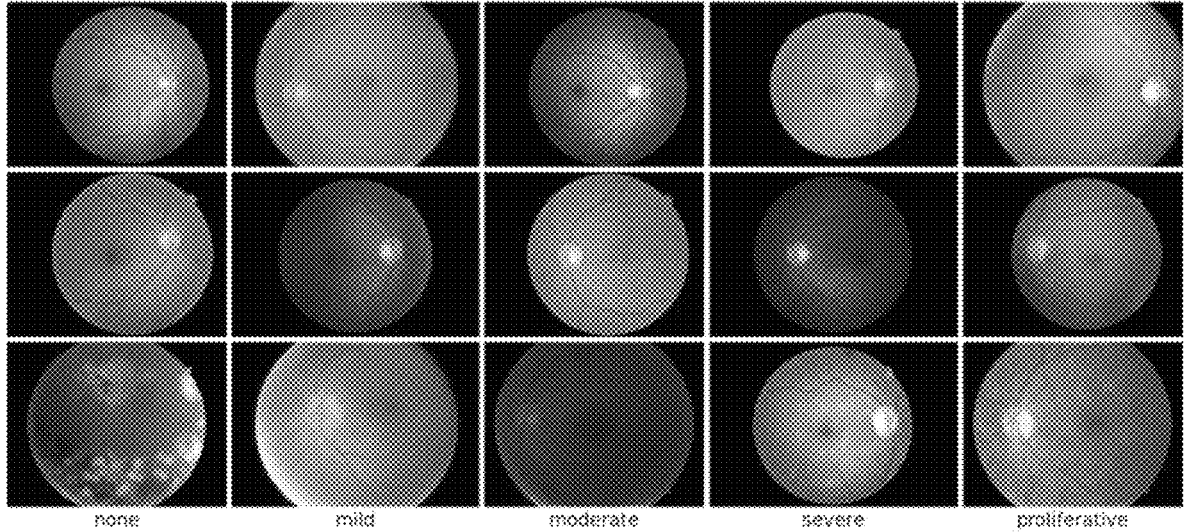
FIG. 3 illustrates an example set of retinal images from the EyePACS dataset corresponding to each of the five gradings of diabetic retinopathy. From left to right, the retinal images are labeled with no diabetic retinopathy, mild diabetic retinopathy, moderate diabetic retinopathy, severe diabetic retinopathy, and proliferative diabetic retinopathy.
Figure 4:
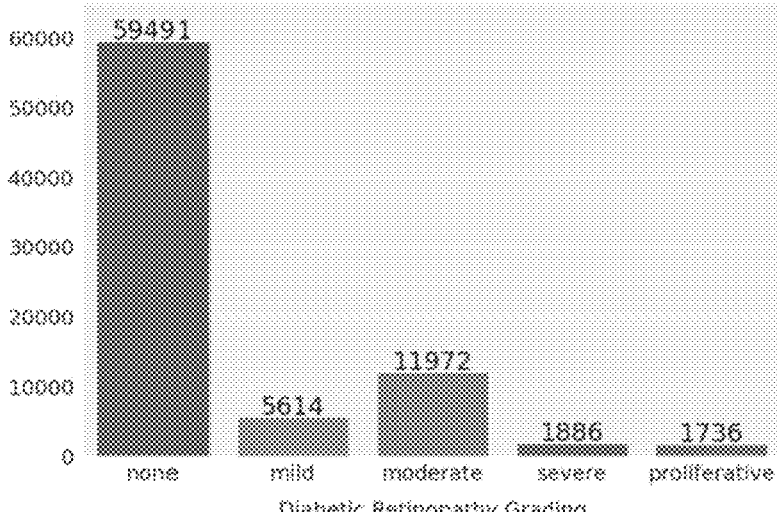
FIG. 4 illustrates a bar chart representing the distribution of image counts for the five different diabetic retinopathy gradings in the EyePACS dataset.

The second dataset ("the EyePACS dataset") was also used, which includes over 80,000 retinal images and a corresponding labels indicating one of the five different gradings dependent on the severity of diabetic retinopathy: (1) none, (2) mild, (3) moderate, (4) severe, and (5) proliferative. Thus, for example, a grading of (2) mild represents that the image of the retina corresponds to a subject with mild diabetic retinopathy. Similar to FIG. 1, FIG. 3 shows randomly selected example images from the EyePACS dataset with retina images at each of the five stages of diabetic retinopathy gradings. FIG. 4 is a graphical representation of the EyePACS dataset with the severity of diabetic retinopathy on the x-axis and the number of participates on the y-axis. For example, the EyePACS dataset include 11,972 retinal images that corresponded to subjects with moderate diabetic retinopathy.

The QBB dataset and the EyePACS dataset were used in an example embodiment of the present disclosure. However, before being used, the present embodiment may process the data, which may include several sub-steps. In an example process, the present embodiment extracts and resizes the circular region from each image. After resizing the image, the radius of the retina is 300 pixels. Next, the present embodiment crops the outer 10% of each image to eliminate the border-noise, which is followed by a subtraction of the local mean from a 4 by 4 pixel neighborhood. Then, the present embodiment places the cropped retina into a dark background inside a square-shaped image with tight borders. The preceding processing steps transform each image in the dataset from a varying sized image to a 570 by 570 image with a black background.

Figure 5:
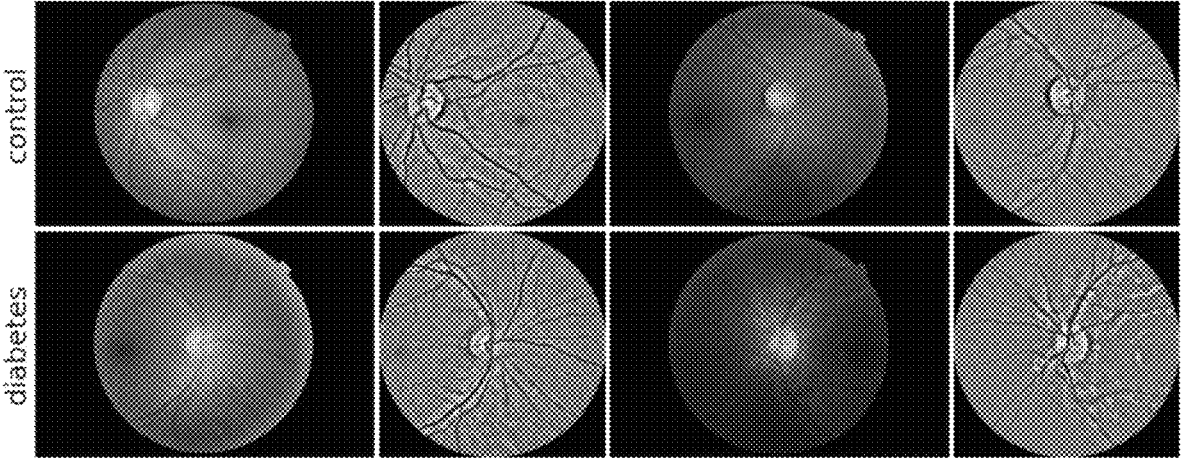
FIG. 5 illustrates an example set of retinal images from the QBB dataset before and after pre-processing. The first and third columns show the raw images before pre-processing, while the second and fourth columns show the corresponding images after pre-processing.

Once the images are aligned with a similar background, the present embodiment may augment the data. Namely, in an example augmentation step, the present embodiment performs a random horizontal flip, a random brightness adjustment, and a random contrast perturbation. The processing and augmentation steps may be completed on each retinal image from the QBB and the EyePACS data set. FIG. 5 illustrates an example set of retinal images from the QBB dataset before and after the processing steps. Starting from left to right, the first and the third columns show the raw images taken from the dataset. Thus, the second and the fourth columns show the corresponding image after the processing steps are complete. After processing and augmenting the data, the present embodiment may be executed.

In an example embodiment, the method starts with an initial model, DenseNet-121, which is referenced as model M0. The method then trains M0 on the ImageNet dataset to a first model, which is referenced as model M1. Unlike M0, M1 is capable of image classification. Next, the method trains model M1 on the EyePACS dataset to yield model M2 for detecting diabetic retinopathy. The task of detecting diabetic retinopathy is defined as the binary task of identifying whether or not a person has diabetic retinopathy.

At the end of this fine-tuning stage, model M2 is used to distinguish between retinal images with diabetic retinopathy and without diabetic retinopathy. However, because the present embodiment cannot differentiate between diabetic and non-diabetic retinal images, model M2 must be further adjusted. Namely, model M2 is fine-tuned on the QBB dataset, which contains retinal images from non-diabetic subjects and diabetic subjects with and without diabetic retinopathy. This step produces a further model, model M3, which can identify diabetic and non-diabetic patients from their retinal images.

As introduced, the proposed model, M3, uses DenseNet as the base Convolutional Neural Network ("CNN"). More specifically, DenseNet is an image classification CNN. The architecture of DenseNet allows training models that are much deeper than AlexNet or VGG, and differs from ResNet in the manner in which the feature maps from the previous layers are combined. For example, in ResNets, feature maps are combined downstream using the addition operation, which means feature maps are summed element-by-element along the channel (feature map) dimension, while in DenseNet, they are concatenated, along the same dimension. This allows a layer in DenseNets to have access to the features from all the previous layers, which aids in improving its performance as decisions can be made based on features extracted from the input image at different scales.

Further, a 121-layer variant of DenseNet was used, which consists of four dense blocks due to its superior performance. This variant is referenced as DenseNet-121. And despite being 121-layer deep, overfitting was not an issue due to (1) the dense connections themselves acting as regularizes and (2) counter-intuitively, the network having less parameters compared to a non-dense CNN.

Figure 6:
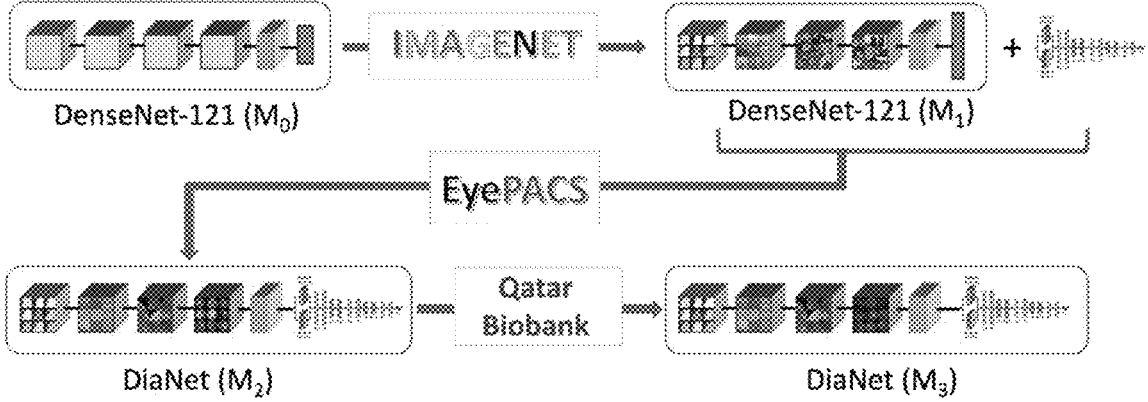
FIG. 6 illustrates an example embodiment of a method of training a convolutional neural network model to predict diabetes from the image of a retina according to embodiments of the present disclosure.

FIG. 6 illustrates an example embodiment of the proposed method. The top left model, M0, is a randomly initialized DenseNet-121 model. Training M0 on the ImageNet dataset yields M1, which is capable of image classification. After adding additional layers and fine-tuning M1 on the EyePACS, retinal image dataset yields M2. As previously stated, M2 includes retinal image understanding capability. Finally, fine-tuning M2 on the QBB dataset results in an example embodiment of the proposed model, M3, which can be used for diabetes detection from retinal images independent of diabetic retinopathy.

Figure 7:
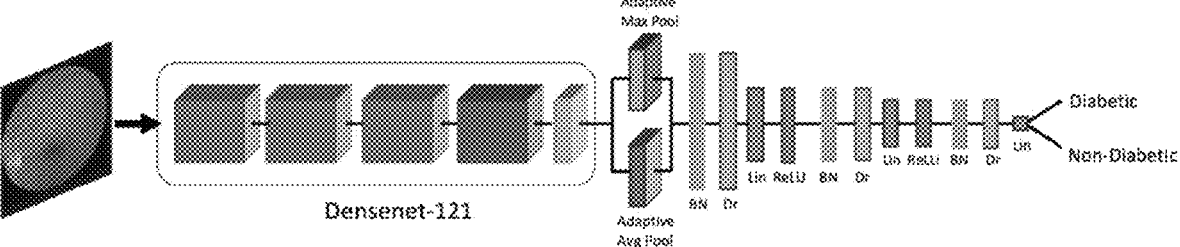
FIG. 7 illustrates an example embodiment of the architecture of the convolutional neural network model to predict diabetes from the image of a retina according to embodiments of the present disclosure, according to embodiments of the present disclosure.

FIG. 7 illustrates the proposed architecture of M3 ("DiaNet"), which consists of a DenseNet-121 backbone and additional layers consisting of a pair of pooling layers followed by three composite layers each consisting of a sequence of a batch normalization layer ("BN"), a dropout layer ("Dr"), a linear layer ("Lin"), and a rectified linear activation function layer ("ReLU"). The final layer contains a single neuron indicating the predicted label (diabetic/non-diabetic). The configurations of these layers can be below found Table 1. As shown below in Table 1, the first two pooling layers were concatenated into a single input of size 2048 for the next layer.

TABLE I

Details of the layers added at the end of Densenet-121 in DiaNet.

| Layer Name | Output Size | Number of Parameters |
|---|---|---|
| AdaptiveMaxPool2D | [1024, 1, 1] | 0 |
| AdaptiveAvgPool2D | [1024, 1, 1] | 0 |
| Flatten + Concat | [2048] | 0 |
| BatchNorm1D | [2048] | 4096 |
| Dropout | [2048] | 0 |
| Linear | [512] | 1,049,088 |
| ReLU | [512] | 0 |
| BatchNorm1D | [512] | 1024 |
| Dropout | [512] | 0 |
| Linear | [256] | 131,328 |
| ReLU | [256] | 0 |
| BatchNorm1D | [256] | 512 |
| Dropout | [256] | 0 |
| Linear | [2] | 512 |

To achieve the proposed architecture of FIG. 7, the vanilla DenseNet-121 network trained on ImageNet has 1,000 neurons in the final layer, corresponding to the number of labels in the dataset. Since diabetes detection is a binary task, the final layer was changed into a 2-neuron layer. Additionally, adding a concatenation of global average pooling layer and a global max pooling layer followed by a series of batch normalization, dropout, linear, and ReLU layers before the final linear layer boosted the performance by over 2%. Table I shows the output shape and number of parameters for each added layer. FIG. 7 shows a detailed diagram of the proposed network architecture referred to as M3 or DiaNet.

To evaluate the performance of the proposed approach and establish baselines, two sets of models were developed. The first set of models is referred to as "DiaNet Variants." DiaNet Variants are based on DiaNet_Res50, which was developed by replacing the backbone of DiaNet with a ResNet50 pre-trained on ImageNet. For the combined approach, activations from the penultimate layer of a CNN were taken used as the input to the GBM, which acts as the classifier. XGBoost ("XGB") was used as the GBM implementation, resulting in two more classification models: DiaNetCXGB and DiaNet_Res50CXGB. After establishing the three DiaNet Variant models, namely: (1) DiaNet_Res50, (2) DiaNetCXGB, and (3) DiaNet_Res50CXGB, each model was fine-tuned in multiple stages. In the first stage, these four models were fine-tuned using the EyePACS dataset and in the second stage on the QBB dataset.

The second set of models is referred to as QBBNet and QBBNet Variants. Unlike DiaNet, only the QBB dataset was considered to develop QBBNet. Similar to DiaNet, QBBNet considered DenseNet-121 and ResNet50 for configuring end-to-end CNNs and their variants with an XGB as the classifier. The models were then fine-tuned only on the QBB dataset. This results in a total of four additional experimental configurations for QBBNet: (1) QBBNet, (2) QBBNet Res50, (3) QBBNetCXGB, and (4) QBBNet Res50CXGB. Thus, including the first set of models, the second set of models, and DiaNet, there are eight total models used for conducting experiments.

Model selection, generalization, and performance estimation in the fine-tuning stage on the QBB dataset were carried out using nested cross-validation to prevent data leakage. A 5-fold setup in both inner and outer folds was used. To obtain even more consistent results, experiments were repeated five times and the arithmetic mean of the representative metrics for reporting was computed. Due to the enormous size of the EyePACS dataset, only a single train-validation-test split in the fine-tuning stage using this dataset was sufficient to ensure that these sets have similar distributions.

The data was pre-processed and augmented using the same approach in multi-stage tuning for DiaNet and single-stage tuning for QBBNet. The Dropout layers added in the networks used 0.4 as the dropout probability. For minimizing the loss, the AdamW optimizer with a One-Cycle Learning Rate Schedular was used.

For multi-stage fine-tuning using the EyePACS and the QBB dataset, models were first trained on the former. To this end, binary labels were created so that non-DR cases and the DR cases (mild, moderate, severe, and proliferative) are the negative and positive classes, respectively. Since the dataset remained severely imbalanced even after this re-labeling, class weights inversely proportional to the number of examples in each class were used. Using a batch size 64 and a maximum one-cycle learning rate of 3e-2, the models were fine-tuned for 20 epochs, which led to convergence of the training and validation loss curves.

After this fine-tuning stage, which completed in approximately 8 hours for DiaNet and 5 hours for DiaNet_Res50, the models on the QBB dataset were fine-tuned. Unlike the previous stage, L2 regularization (with the regularization constant set to 0.02) was needed to prevent overfitting, which is expected given the small size of the dataset. Each model was fine-tuned with a batch size of 32 for: (a) 30 epochs keeping everything but the added layers frozen, using a maximum one-cycle learning rate of 1e-4, then (b) $2o$ epochs unfreezing the entire network and training using discriminative learning rates with the following range: (1e-5 and 1e-7). DiaNet and DiaNet_Res50 took 3 and 1.5 hours to complete training over these 50 epochs, respectively. Since QBB dataset is balanced, there was no need to employ any technique to compensate for any imbalance, such as class weights that were used in the earlier stage.

For the single-stage fine-tuning experiments conducted solely on the QBB dataset, the use of L2 regularization (with the regularization constant set to 0.01) prevented overfitting. The rest of the parameter values were identical to those used in the latter stage of our multi-stage fine-tuning experiment.

Once the experiments were complete, the performance of DiaNet was quantitatively compared against other candidate methods, which demonstrated its superiority in predicting the onset of diabetes among the test subjects. For quantitative performance reporting, mean accuracy, sensitivity, specificity, precision, F1 score and AUC ROC were used. Since QBB dataset is balanced, using the mean accuracy as the measure of model assessment suffices.

As an overview of the performances of the methods experimented on, Table II shows the corresponding accuracies and other evaluation metrics. DiaNet fine-tuned on the EyePACS and the QBB dataset performed best with an 84.47% mean accuracy. In comparison, QBBNet, which was trained only on the smaller, QBB dataset, yields 79.02% accuracy. It could be mentioned that the base architecture of DiaNet (Densenet-121) achieved only 80% accuracy on the EyePACS test dataset. This shows that, even though the EyePACS dataset is targeted to a task (DR staging), the network benefitted from the first-stage fine-tuning as it helped the network understand from a larger dataset what retina images look like and transfer that knowledge to our task.

TABLE II

| Performance of different candidate model variants for DiaNet and QBBNet. | | | | | | |
|---|---|---|---|---|---|---|
| Metric | Accuracy | Precision | Sensitivty/Recall | Specificity | F1 Score | AUC ROC |
| QBBNet_Res50 + XGB | 80.65 | 79.27 | 83.15 | 78.14 | 81.16 | 80.64 |
| DiaNet_Res50 + XGB | 82.01 | 80.41 | 84.78 | 76.23 | 82.53 | 82.08 |
| QBBNet + XGB | 76.56 | 76.63 | 76.63 | 76.5 | 76.63 | 76.56 |
| DiaNet + XGB | 83.92 | 81.09 | 82.58 | 79.23 | 84.67 | 83.91 |
| QBBNet_Res50 | 80.38 | 80.94 | 76.63 | 79.15 | 79.66 | 80.39 |
| DiaNet_Res50 | 83.1 | 81.77 | 85.32 | 80.87 | 83.51 | 83.1 |

TABLE II-continued

| Performance of different candidate model variants for DiaNet and QBBNet. | | | | | | |
| --- | --- | --- | --- | --- | --- | --- |
| Metric | Accuracy | Precision | Sensitivty/Recall | Specificity | F1 Score | AUC ROC |
| QBBNet | 79.02 | 78.01 | 30.97 | 77.04 | 79.47 | 79.01 |
| DiaNet | 84.47 | 83.59 | 85.86 | 83.06 | 84.71 | 84.46 |

Figure 8:
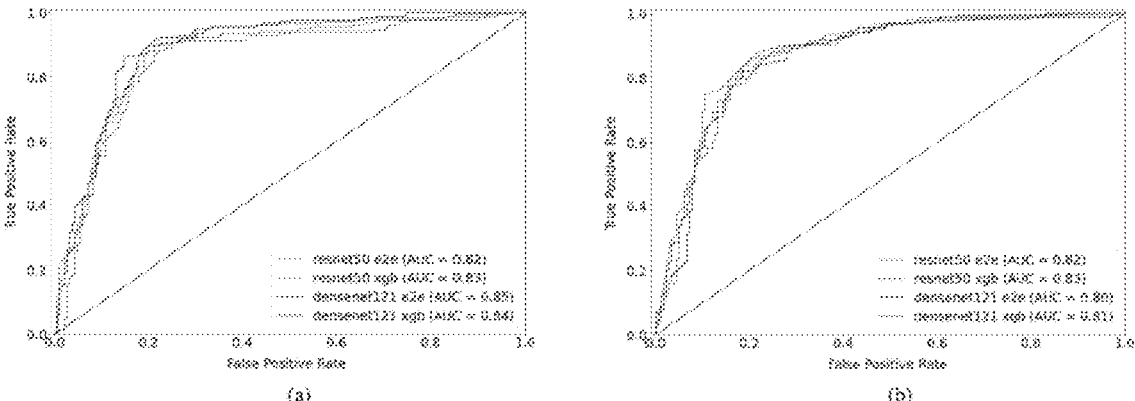
FIG. 8, which includes views (a) to (b), illustrates example ROC plots for the classifiers, according to embodiments of the present disclosure.

Table II supports the conclusion that DiaNet uses an effective transfer learning technique, which entails first training a neural network on a large dataset to train it with domain knowledge, then fine-tuning it on a dataset aimed at a slightly different, but related task. Table II also shows that the highest F1 score of 84.71 and 79.47 from DiaNet and QBBNet, respectively. Lastly, FIG. 8 highlights the ROC curves for both QBBNet and DiaNet. The highest AUC for the DiaNet and QBBNet was 84.4 and 83.10, respectively.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

I claim:

1. A method of training a convolutional neural network model to predict diabetes from an image of a retina, comprising:
   processing a first dataset, wherein processing the first dataset comprises:
   extracting a circular region from a retinal image;
   resizing the circular region;
   cropping the circular region; and
   placing the circular region onto a black background;
   training an initial model using a second dataset to yield a first model;
   training the first model using a third dataset to yield a second model; and
   training the second model using the first dataset to yield a third model-,
   wherein the third dataset comprises a plurality of retinal images labeled based on the severity of diabetic retinopathy.

2. The method of training a convolutional neural network model to predict diabetes from the image of a retina of claim 1, wherein processing the first dataset outputs an image having a retina with a radius of 300 pixels.

3. The method of training a convolutional neural network model to predict diabetes from the image of a retina of claim 1, wherein the initial model is a DenseNet model.

4. The method of training a convolutional neural network model to predict diabetes from the image of a retina of claim 3, wherein the DenseNet model is a 121-layer variant DenseNet model.

5. The method of training a convolutional neural network model to predict diabetes from the image of a retina of claim 1, wherein the first dataset comprises a plurality of retinal images including a first group of retinal images and a second group of retinal images.

6. The method of training a convolutional neural network model to predict diabetes from the image of a retina of claim 5, wherein the first group of retinal images relates to a control group and the second group of retinal images relates to a diabetes group.

7. A convolutional neural network model architecture to predict diabetes from an image of a retina, comprising:
   a DenseNet-121 backbone;
   a final layer outputting a predictive label corresponding to a diabetic prediction or a non-diabetic prediction;
   a pair of pooling layers; and
   a first composite layer, a second composite layer, and a third composite layer,
   wherein the pair of pooling layers comprise a global average pooling layer and a global max pooling layer.

8. The convolutional neural network model architecture of claim 7, wherein the final layer is a single neuron layer.

9. The convolutional neural network model architecture of claim 7, wherein the first composite layer comprises a first sequence of a plurality of layers, the second composite layer comprises a second sequence of a plurality of layers, and the third composite layer comprises a third sequence of a plurality of layers.

10. The convolutional neural network model architecture of claim 9, wherein the first sequence of the plurality of layers comprises a batch normalization layer, a dropout layer, a linear layer, and a rectified linear unit layer.

11. The convolutional neural network model architecture of claim 9, wherein the second sequence of the plurality of layers comprises a batch normalization layer, a dropout layer, a linear layer, and a rectified linear unit layer.

12. The convolutional neural network model architecture of claim 9, wherein the third sequence of the plurality of layers comprises a batch normalization layer, a dropout layer, and the final layer for outputting the predictive label.

13. A method of training a convolutional neural network model to predict diabetes from the image of a retina, comprising:
   processing a first dataset and a second dataset, wherein processing the first dataset and the second dataset comprises:
   extracting a circular region from a retinal image;
   resizing the circular region;
   cropping the circular region; and
   placing the circular region onto a black background;
   training a DenseNet-121 model using an third dataset to yield a first model;
   training the first model using the second dataset to yield a second model; and training the second model using the first dataset to yield
    a third model,
wherein the third model has an architecture comprising:
    a DenseNet-121 backbone;
    a global average pooling layer;
    a global max pooling layer;
    a first composite layer;
    a second composite layer; and
    a third composite layer.

14. The method of training a convolutional neural network model to predict diabetes from the image of a retina of claim 13, wherein the third composite layer comprises:
    a batch normalization layer,
    a dropout layer; and
    a final layer outputting a predictive label corresponding to
        a diabetic prediction or a non-diabetic prediction.

15. The method of training a convolutional neural network model to predict diabetes from the image of a retina of claim 13, wherein the first composite layer comprises:
    a batch normalization layer;
    a dropout layer;
    a linear layer; and
    a rectified linear unit layer.

* * * * *